United States Patent [19]

Vogt

[11] 4,070,355
[45] Jan. 24, 1978

[54] 1,5-BENZODIAZEPIN-2-ONES

[75] Inventor: B. Richard Vogt, Yardley, Pa.

[73] Assignee: E. R. Squibb & Sons, Inc., Princeton, N.J.

[21] Appl. No.: 778,531

[22] Filed: Mar. 17, 1977

Related U.S. Application Data

[62] Division of Ser. No. 404,071, Oct. 5, 1973, Pat. No. 4,033,947.

[51] Int. Cl.² ............... C07D 487/22; C07D 243/12
[52] U.S. Cl. ............... 260/239.3 B; 260/239.3 T; 424/269
[58] Field of Search ............... 260/239.3 B

[56] References Cited

U.S. PATENT DOCUMENTS 4,033,947  7/1977  Vogt ............... 260/239.3 T

FOREIGN PATENT DOCUMENTS 2,306,770  9/1974  Germany ............... 260/239.3 B
2,447,731  4/1975  Germany ............... 260/239.3 B Primary Examiner—Henry R. Jiles
Assistant Examiner—Robert T. Bond
Attorney, Agent, or Firm—Lawrence S. Levinson; Merle J. Smith; Burton Rodney

[57] ABSTRACT

Compounds of the formula

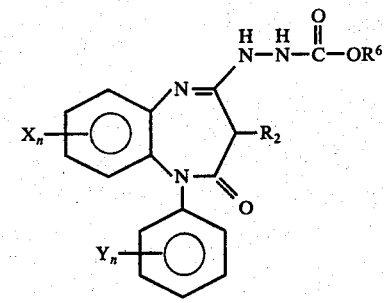

which are useful intermediates in the preparation of compounds of the formula

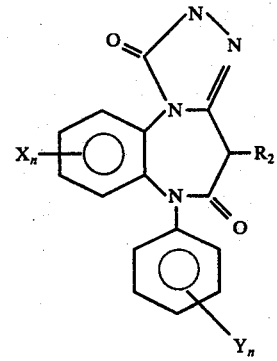

which are useful as central nervous system depressants, tranquilizers, sedatives and muscle relaxants.

6 Claims, No Drawings

1,5-BENZODIAZEPIN-2-ONES

RELATED APPLICATION

This is a divisional application of application Ser. No. 404,071 as filed Oct. 5, 1973, now U.S. Pat. No. 4,033,947.

OBJECTS OF THE INVENTION

It is an object of the present invention to provide new compounds which are useful as central nervous system depressants, tranquilizers, sedatives and muscle relaxants. Another object is to provide methods for the preparation of these compounds. Another object is to provide compositions for the administration of the compounds of the invention. These and other objects of the present invention will be apparent from the following description.

SUMMARY OF THE INVENTION

It has now been found that 1H-s-triazolo[4,3-a][1,5]benzodiazepin-1,5(6H)-diones of the following formula

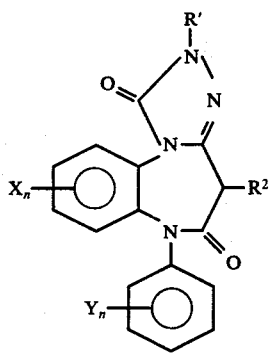

are useful CNS depressants, tranquilizers, sedatives, and muscle relaxants in mammalian species.

DETAILED DESCRIPTION

The novel 1H-s-triazolo[4,3-a][1,5]benzodiazepin-1,5(6H)-diones of formula 1 are useful CNS depressants, tranquilizers and sedatives. The compounds of formulas 3-12, and the novel compounds of formula 7 are intermediates for the compounds of formula 1.

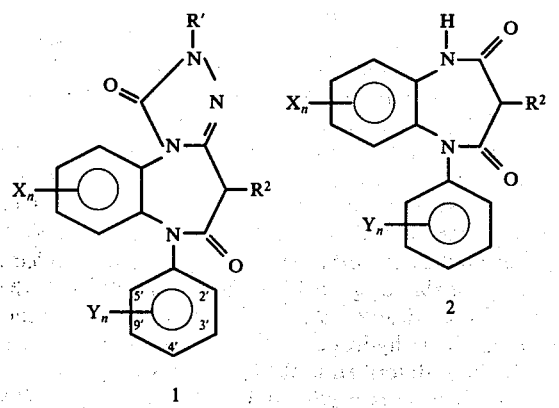

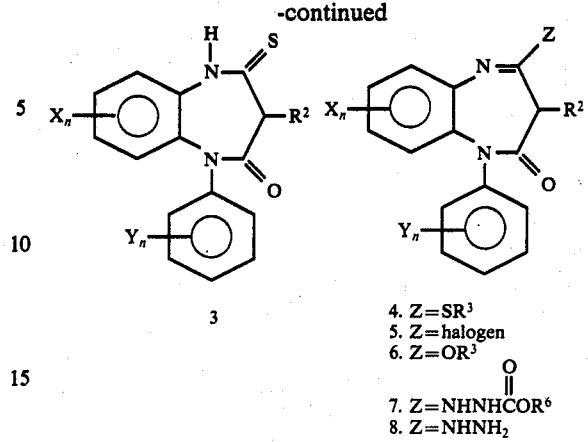

4. $Z=SR^3$
5. $Z=$halogen
6. $Z=OR^3$
7. $Z=NHNHCOR^6$
8. $Z=NHNH_2$

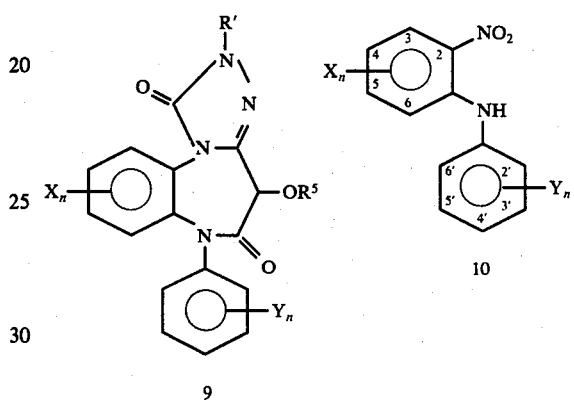

In the foregoing formulas $R^1$ is H; alkyl of 1-3 carbons optionally substituted by amino, by mono-alkyl wherein the alkyl radical contains 1-3 carbons, by dialkylamino wherein the alkyl radicals contain 1-3 carbons, by phenyl wherein the phenyl ring is optionally substituted by one or more D groups wherein D is as defined below; or phenyl wherein the phenyl ring is optionally substituted by one or more D groups wherein D is as defined below;

$R^2$ is H, alkyl of 1-3 carbons, hydroxy or acyloxy (1-4 carbons).

X and Y can be the same or different and are hydrogen, F, Cl, Br, trifluromethyl, alkyl of from 1-4 carbons, alkoxy of from 1-4 carbons, nitro, cyano, amino, alkanoylamino of 1-4 carbons, alkylthio of 1-4carbons, alkylsulfinyl of 1-4 carbons or alkyl sulfonyl of 1-4 carbons;

D can be alkyl of 1-3 carbons; halogen, preferably bromine and chlorine; trifluoromethyl; alkoxy of 1-3 carbons; and nitro.

$R^4$ is alkyl of 1-3 carbons optionally substituted by amino, monalkylamino of 1-3 carbons, dialkylamino of 1-3 carbons, and phenyl wherein the phenyl ring is optionally substituted by one or more groups as defined for D.

$R^3$ is alkyl of from 1-4 carbons, benzyl or phenethyl;

n is 0, 1 or 2;

$R^5$ is a group of formula

where P and Q may be the same or different and may be hydrogen or phenyl optionally substituted by one or more groups as defined for D, with the proviso that at least one of P and Q is aryl.

$R^6$ is alkyl of 1–4 carbons optionally substituted by phenyl.

SYNTHESIS

The 1H-s-triazolo[4,3-a][1,4]benzodiazepin-1,5(6H)-diones of formula 1 can be prepared by several methods.

One method (hereinafter called the first method) for the synthesis of compounds wherein R' is hydrogen involves reacting a compound of formulas 3–6 with from about 0.8 to about 6.0, preferably from about 1.0 to about 3.0 molar equivalents of an alkyl carbazate of formula

R⁶OCNHNH₂

(where $R^6$ is as defined previously) either along or, preferably, in an inert, organic solvent or mixture of solvents. Typical organic solvents which may be used in the above reaction include aryl hydrocarbons, e.g., benzene, toluene, xylene and the like; chlorinated hydrocarbons such as di-, tri-, tetrachloroethanes and the like; lower molecular weight alkanols of 1–4 carbons such as ethanol, tertiary butyl alcohol, n-butanol and the like; N,N-dialkylformamides, N,N-dialkylalkanoyl amides wherein the alkyl and alkanoyl radicals have 1–4 carbons, such as dimethylformamide, dimethylacetamide and the like; hexamethylphosphorous triamide, ethers, such as dioxane and the like and di-lower alkyl sulfoxides, such as dimethyl sulfoxide and the like. The reaction is carried out at from about 40° C to about 320° C, preferably from about 80° C to about 250° C, until a significant amount of end product is obtained, typically, for from about ¼ to about 92 hours, preferably from about 1 to about 48 hours.

The final product of formula 1 wherein R' is hydrogen is isolated by conventional techniques. For example, the reaction mixture is evaporated and the residue is partitioned between aqueous sodium bicarbonate and a water-immiscible inert, organic solvent, such as halogenated hydrocarbons, e.g., methylene chloride, chloroform or trichloroethylene; alkyl esters wherein both the acid and alcohol from which the ester is derived may have from 1 to 4 carbon atoms, e.g., ethyl acetate, propyl acetate, ethyl propionate and the like. The organic solvent is washed with water, dried and chromatographed.

Another method for the synthesis of compounds of formula 1 wherein R' is hydrogen involves heating compounds of formula 7 either alone or in an inert, organic solvent at from about 60° C to about 350° C, preferably from about 80° C to about 300° C for from about ½ to about 72 hours, preferably from about 1/6 to about 12 hours. Typical inert, organic solvents that are used are those defined in the first method. The products are isolated by conventional techniques. For example, the reaction is diluted with a water-immiscible, inert, organic solvent, washed with water, dried and chromatographed.

Another method (hereinafter called the third method) of synthesis for compounds of formula 1 wherein R' is hydrogen involves reacting compounds of formula 8 with from about 0.8 to about 6, preferably from about 1 to about 3, molar equivalents of acyl derivatives of formula

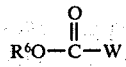
R⁶O—C—W (where W is —OR⁶ or halogen, preferably chlorine or bromine), in the presence of a tertiary amine base in an optional inert organic solvent. Typical inert organic solvents which may be used include aryl hydrocarbons such as benzene, toluene, xylene and the like; chlorinated hydrocarbons such as tri- and tetrachloroethanes and the like; ethers such as 1,2-dimethoxyethane, tetrahydrofuran, dioxane and the like; N,N-dialkylformamides and N,N-dialkyl alkanoylamides wherein the alkyl and alkanoyl radicals have 1–4 carbons such as dimethylformamide, dimethylacetamide and the like. Typical tertiary bases include pyridine and the like and triethylamine and the like. The reaction conditions and the isolation of the products are as described in the first method.

Compounds of formula 1 where R' is alkyl of 1–3 carbons substituted by amino, by mono-alkylamino of 1–3 carbons, by di-alkylamino of 1–3 carbons or by phenyl optionally substituted by one or more D groups, are prepared by reacting compounds of formula 1 where R' is hydrogen with from about 0.5 to about 12, preferably from about 0.8 to about 1.2 molar equivalents of an appropriate base, followed by reaction of the thus formed salt with a corresponding molar equivalent of an appropriate substituted alkylating agent of formula $R^4$—M where $R^4$ is as defined previously and M is halogen, preferably chlorine, bromine, iodine;

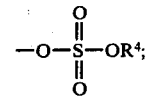
—O—S—OR⁴;

or an alkyl or arylsulfonate of formula

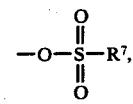
—O—S—R⁷, where $R^7$ can be alkyl of 1–6 carbons or aryl of from about 6 to 10 carbons optionally substituted by halogen, nitro or alkyl of 1 to 3 carbons, or $R^4$—M may be any other alkylating agent (within the definition of $R^4$) capable of introducing a group as defined for $R^4$. The reaction is run in an essentially inert organic solvent.

Typical bases include alkali metal (preferably sodium and potassium) salts as well as thallous salts of lower molecular weight alkanols of 1–6 carbons such as methanol, ethanol, propanol, isopropal, t-butanol, amyl alcohol and the like; alkali metal (preferably sodium) hydrides; alkali metals (preferably sodium and potassium); alkali metal (preferably sodium and potassium) salts of acidic hydrocarbons such as triphenylmethane and the like as well as any other base known to those skilled in the art capable of generating salts of the acidic hydrogen of the triazole ring in compounds of formula 1 wherein R' is hydrogen. Typical organic solvents include those described in the first method.

The reaction is carried out at from about 20° C to about 300° C, preferably from about 0° C to about 100°

C for from about 0.2 hour to about 96 hours, preferably from about 0.5 hour to about 72 hours.

The products are isolated by conventional techniques. For example the reaction mixture is evaporated; the residue is diluted with a water-immiscible, inert solvent such as methylene chloride, washed with water, dried and chromatographed.

Compounds of formula 1 wherein R' is phenyl or substituted phenyl can be prepared by reacting compounds of formula 1 wherein R' is hydrogen with at least from about 0.5 to a large excess, preferably at least from about 0.8 to about 100, molar equivalents of a phenyl halide, in the presence of a copper catalyst, in an optional solvent containing from about 0.5 to about 1000, preferably from about 0.8 to about 100, molar equivalents of an appropriate hydrogen halide acceptor. The preferred phenyl halides are those of formula AR—K where AR is phenyl optionally substituted by one or more groups as defined for D and where K is preferably chlorine, bromine or iodine. The preferred copper catalysts are powdered copper metal, copper oxides and cuprous and cupric salts. Optional solvents include N,N-dialkylformamides and N,N-dialkyl alkanoyl amides wherein the alkyl and alkanoyl radicals have 1-4 carbons such as N,N-dimethylformamide, N,N-dimethylacetamide and the like; dialkyl sulfoxides of 2-6 carbons such as dimethyl sulfoxide and the like; and alkylphosphorous triamides of 4-10 carbons such as hexamethylphosphorous triamide. Appropriate hydrogen halide acceptors include alkali metal (preferably sodium or potassium) carbonates, bicarbonates, or lower alkyl carboxylic acid salts thereof (e.g., acetates). The reaction is carried out at from about 50° C to about 200° C, preferably at from about 90° C to about 180° C, for from about ¼ to about 72 hours, preferably for from about ½ to about 14 hours. The product is isolated in a conventional manner. For example, the reaction mixture is diluted with methylene chloride, washed with dilute aqueous ammonium hydroxide and chromatographed.

Compounds of formula 1 where R² is hydroxy are prepared by reacting compounds of formula 9 with hydrogen in the presence of an appropriate catalyst, in an inert organic solvent. Typical catalysts include platinum, Raney nickel and, preferably, palladium Typical solvents include lower alkanols of 1-4 carbons such as methanol, ethanol, and the like; formic acid; lower alkanoic acids of 2-5 carbons such as acetic acid and the like as well as other typical solvents well known to those versed in the art. Typical hydrogenation pressures are from about 0.1 to about 2000 atmospheres, preferably from about 0.8 to about 100 atmospheres. The reactions are carried out for from about ½ to about 96 hours, preferably from about 1 to about 72 hours at from about 0° C to about 200° C, preferably from about 20° C to about 120° C. The products are isolated in a conventional manner. For example the catalyst is filtered off, the solvent evaporated and the product chromatographed.

Compounds of formula 1 wherein R² is acyl of 1-4 carbons are prepared by reacting compounds of formula 1 wherein R² is hydroxy with from about 0.8 to about 6, preferably from about 1 to about 3, molar equivalents of acyl derivatives of formula

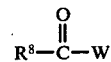

(where R⁸ is alkyl of from 1-3 carbons and W is halogen, preferably chlorine or bromine or

either alone or optionally in an inert organic solvent, in the optional presence of a tertiary amine. Typical inert organic solvents which may be used include aryl hydrocarbons such as benzene, toluene, xylene and the like; chlorinated hydrocarbons such as tri- and tetrachlorethanes and the like; ethers such as 1,2-dimethoxyethane, tetrahydrofuran, dioxane and the like; N,N-dialkylformamides and N,N-dialkyl alkanoylamides wherein the alkyl and alkanoyl radicals have 1-4 carbons such as dimethylformamide, dimethylacetamide and the like. Typical tertiary amines include heterocyclic amines such as pyridine and the like and trialkyl amines wherein each alkyl radical has from 1-4 carbon atoms such as triethylamine and the like. The reaction conditions and the isolation of the products are as described in the first method.

Compounds of formula 7 are prepared by reacting compounds of formulas 3-6 with from about 0.8 to about 6.0, preferably with from about 1 to about 3, molar equivalents of an alkyl carbazate of formula

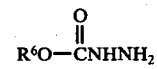

in an inert organic solvent. Typical solvents include alkanols of 1-4 carbons such as methanol, ethanol, t-butanol, n-butanol and the like; aromatic hydrocarbons such as benzene, toluene, xylene and the like; chlorinated hydrocarbons such as methylene chloride, chloroform, di-, tri- and tetrachloroethane and the like; ethers such as tetrahydrofuran, dioxane, 1,2-dimethoxyethane and the like; N,N-dialkylformamides, N,N-dialkyl alkanoyl amides wherein the alkyl and alkanoyl radicals have from 1-4 carbons, such as N,N-dimethyl formamide, N,N-dimethylacetamide and the like; hexamethylenephosphorous triamide and dimethyl sulfoxide. The reaction is carried out at from about −30° C to about 160° C preferably at from about 30° C to about 120° C, until a significant amount of end product is obtained, for from about ½ to about 96 hours, preferably for from about 2 to about 12 hours. The products of formula 7 are isolated by conventional techniques. For example, the reaction is diluted with a water-immiscible inert organic solvent, washed with water, dried and chromatographed.

Another method for the synthesis of compounds of formula 7 involves reacting compounds of formula 8 with from about 0.5 to about 6, preferably from about 0.8 to about 1.2, molar equivalents of acyl derivatives of formula

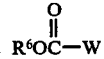

(where W is as defined previously) in an optional inert organic solvent, in the optional presence of a tertiary amine.

Typical tertiary amines include heterocyclic amines such as pyridine and the like and trialkylamines such as triethylamine and the like.

Typical inert organic solvents include those described for the third method.

The reaction is carried out at from about −30° C to about 150° C, preferably from about 0° C to about 80° C for from about ¼ hour to about 72 hours, preferably from about ½ hour to about 14 hours.

The products of formula 7 are isolated by conventional techniques as, for example, described in the first method.

The starting materials of formulas 3–6 and 8 are described in patent application Ser. No. 365,012 and references cited therein.

The novel compounds of formula 1 are CNS depressants and are useful as, for example, sedatives, tranquilizers and muscle relaxants in mammalian species, e.g., rats, mice and monkeys. Thus, for example, oral administration of a compound of the invention produces ataxia dosage levels of from about 50 to about 200 mg/kg, specifically in rats at about 100 mg/kg.

The compounds of the present invention produce decreased grip strength at a dosage level of from about 5 to about 50 mg/kg, specifically at a dosage level of about 12 mg/kg when administered orally to rats.

The compounds of the present invention have a tranquilizing effect when administered orally at a dosage level of from about 2 to about 25 mg/kg, specifically at a dosage level of about 12 mg/kg when administered via the oral route to rats in a conflict test procedure [cf. J. R. Vogel, B. Beer, D. Clody, Psychopharmacologist 21, 1 (1970)].

The compounds of the present invention in the described dosages may be administered orally; however, other routes such as intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

In the following examples all reactions are run under an inert atmosphere (e.g., argon), at room temperature, using anhydrous solvents unless otherwise indicated; in addition, reactions which are heated are subsequently cooled to room temperature for work-up. In general, solvents are evaporated in a rotary flash vacuum apparatus. In this patent application, the full name of the parent ring system of compounds described as indicated in Column I below is as indicated in Column II.

| I | II |
|---|---|
| "---1H-s-triazolo[4,3-a][1,5]-benzodiazepine-1,5-dione---" | "---2,4,5,6-tetrahydro-1H-s-triazolo[4,3-a][1,5]-benzodiazepine-1,5-dione---" |
| "---1H-1,5-benzodiazepin---" | "---2,3,4,5-tetrahydro-1H-1,5-benzodiazepin---" |
| "---3H-1,5-benzodiazepin---" | "---4,5-dihydro-3H-1,5-benzodiazepin---" |

EXAMPLE 1

8-chloro-6-phenyl-1H-s-triazolo[4,3-a][1,5]benzodiazepine-1,5-dione

Method A 30.2 g of 7-chloro-5-phenyl-1H-1,5-benzodiazepin-4-one-2-thione and 33.4 g of ethyl carbazate in 600 ml dimethylformamide are refluxed with stirring for 24 hours. During this time, argon is bubbled through the reaction mixture. The reaction is evaporated in vacuo and the title compound is obtained as described in Example 1, Method B.

Method B 7.50 g of 2-(methylthio)-7-chloro-5-phenyl-3H-1,5-benzodiazepin-4-one and 6.27 g of ethyl carbazate are refluxed in dry dimethylformamide (300 ml) while a slow stream of argon is passed through. After 24 hours, the reaction mixture is evaporated to dryness, azeotroped with benzene and triturated with water (25 ml). The precipitates that formed are filtered off and dried. This material is chromatographed on a florisil column (10 g) eluting successively with methylene chloride (60 ml), CH$_2$Cl$_2$:EtOAc (6:4, 90 ml) and ethyl acetate (75 ml). The fractions containing the product are combined and evaporated to give the title compound. The product is recrystallized from ethyl acetate-hexane.

Method C 3.0 g of 2,7-dichloro-5-phenyl-3H-1,5-benzodiazepin-4-one and 2.5 g of ethyl carbazate in 50 ml of dioxane are refluxed under argon for 24 hours. 2 ml of water is then added, the reaction stirred for 1 hour and the solvent evaporated. The residue is taken up in methylene chloride, washed with dilute aqueous sodium bicarbonate, with water and dried. The solvent is evaporated and the residue is chromatographed on 10–1000μ silica gel thick layer plates (20 × 20 cm) with ethyl acetate-ethanol (9:1) as eluant. The main band, having an approximate Rf range of 0.12–0.28, is removed, stirred with acetone-methanol (9:1) and the silica gel filtered off. The filtrate is evaporated to give the title compound.

Method D

Following the procedure of Example 1, Method B, but substituting 15 g of 2-methoxy-7-chloro-5-phenyl-3H-1,5-benzodiazepin-4-one for 15.8 g of 2-(methylthio)-7-chloro-5-phenyl-3H-1,5-benzodiazepin-4-one in Example 1, Method B, the title compound is obtained.

Method E 3 g of 3-(7-chloro-5-phenyl-3H-1,5-benzodiazepin-4-one-2-yl) carbazic acid ethyl ester is heated at approximately 50° C above its melting point under argon for 25 minutes. The reaction is cooled, dissolved in methylene chloride and purified by column chromatography as described under Method B above to give the title compound.

EXAMPLES 2-27

Following the procedure of Example 1, Method B, but substituting the compounds indicated in Column I below for 2-(methylthio)-7-chloro-5-phenyl-3H-1,5-benzodiazepin-4-one in Example 1, Method B, the compounds indicated in Column II are obtained.

| | I | II |
|---|---|---|
| 2. | 2-(methylthio)-5-phenyl-3H-1,5-benzodiazepin-4-one | 6-phenyl-1H-s-triazolo-[4,3-a][1,5]-benzodiazepine-1,5-dione |
| 3. | 2-(methylthio)-7-trifluoromethyl-5-phenyl-3H-1,5-benzodiazepin-4-one | 8-(trifluoromethyl)-6-phenyl-1H-s-triazolo[4,3-a][1,5]-benzodiazepine-1,5-dione |
| 4. | 2-(methylthio)-7-nitro-5-phenyl-3H-1,5-benzodiazepin-4-one | 8-nitro-6-phenyl-1H-s-triazolo[4,3-a][1,5]-benzodiazepine-1,5-dione |
| 5. | 2-(methylthio)-7-methyl-5-phenyl-3H-1,5-benzodiazepin-4-one | 8-methyl-6-phenyl-1H-s-triazolo[4,3-a][1,5]-benzodiazepine-1,5-dione |
| 6. | 2-(methylthio)-7-methoxy-5-phenyl-3H-1,5-benzodiazepin-4-one | 8-methoxy-6-phenyl-1H-s-triazolo[4,3-a][1,5]benzodiazepine-1,5-dione |
| 7. | 2-(methylthio)-7-(methylthio)-5-phenyl-3H-1,5-benzodiazepin-4-one | 8-(methylthio)-6-phenyl-1H-s-triazolo[4,3-a][1,5]-benzodiazepine-1,5-dione |
| 8. | 2-(methylthio)-7-pentyl-5-phenyl-3H-1,5-benzodiazepin-4-one | 8-pentyl-6-phenyl-1H-s-triazolo[4,3-a][1,5]benzodiazepine-1,5-dione |
| 9. | 2-(methylthio)-7-pentoxy-5-phenyl-3H-1,5-benzodiazepin-4-one | 8-pentoxy-6-phenyl-1H-s-triazolo[4,3-a][1,5]-benzodiazepine-1,5-dione |
| 10. | 2-(methylthio)-7-bromo-5-phenyl-3H-1,5-benzodiazepin-4-one | 8-bromo-6-phenyl-1H-s-triazolo[4,3-a][1,5]benzodiazepine-1,5-dione |
| 11. | 2-(methylthio)-7-fluoro-5-phenyl-3H-1,5-benzodiazepin-4-one | 8-fluoro-6-phenyl-1H-s-triazolo[4,3-a][1,5]-benzodiazepine-1,5-dione |
| 12. | 2-(methylthio)-7-cyano-5-phenyl-3H-1,5-benzodiazepin-4-one | 8-cyano-6-phenyl-1H-s-triazolo[4,3-a][1,5]-benzodiazepine-1,5-dione |
| 13. | 2-(ethylthio)-7-chloro-5-phenyl-3H-1,5-benzodiazepin-4-one | 8-chloro-6-phenyl-1H-s-triazolo[4,3-a][1,5]-benzodiazepine-1,5-dione |
| 14. | 2-(methylthio)-7-chloro-5-(2-fluorophenyl)-3H-1,5-benzodiazepin-4-one | 8-chloro-6-(2-fluorophenyl)-1H-s-triazolo[4,3-a][1,5]-benzodiazepine-1,5-dione |
| 15. | 2-(methylthio)-7-chloro-5-(3-chlorophenyl)-3H-1,5-benzodiazepin-4-one | 8-chloro-6-(3-chlorophenyl)-1H-s-triazolo[4,3-a][1,5]-benzodiazepine-1,5-dione |
| 16. | 2-(methylthio)-7-chloro-5-(4-chlorophenyl)-3H-1,5-benzodiazepin-4-one | 8-chloro-6-(4-chlorophenyl)-1H-s-triazolo[4,3-1][1,5]-benzodiazepine-1,5-dione |
| 17. | 2-(methylthio)-7-chloro-5-(2-methoxyphenyl)-3H-1,5-benzodiazepin-4-one | 8-chloro-6-(2-methoxyphenyl)-1H-s-triazolo[4,3-a][1,5]-benzodiazepine-1,5-dione |
| 18. | 2-(methylthio)-7-chloro-5-(3-methoxyphenyl)-3H-1,5-benzodiazepin-4-one | 8-chloro-6-(3-methoxyphenyl)-1H-s-triazolo[4,3-a][1,5]-benzodiazepine-1,5-dione |
| 19. | 2-(methylthio)-7-chloro-5-(2-methylphenyl)-3H-1,5-benzodiazepin-4-one | 8-chloro-6-(2-methylphenyl)-1H-s-triazolo[4,3-a][1,5]-benzodiazepine-1,5-dione |
| 20. | 2-(methylthio)-7-chloro-5-(3-methylphenyl)-3H-1,5-benzodiazepin-4-one | 8-chloro-6-(3-methylphenyl)-1H-s-triazolo[4,3-a][1,5]-benzodiazepine-1,5-dione |
| 21. | 2-(methylthio)-7-chloro-5-(4-methylphenyl)-3H-1,5-benzodiazepin-4-one | 8-chloro-6-(4-methylphenyl)-1H-s-triazolo[4,3-a][1,5]-benzodiazepine-1,5-dione |
| 22. | 2-(methylthio)-3-methyl-7-chloro-5-phenyl-3H-1,5-benzodiazepin-4-one | 4-methyl-8-chloro-6-phenyl-1H-s-triazolo[4,3-a][1,5]-benzodiazepin-1,5-dione |
| 23. | 2-(methylthio)-3-(benzyloxy)-7-chloro-5-phenyl-3H-1,5-benzodiazepin-4-one | 4-(benzyloxy)-8-chloro-6-phenyl-1H-s-triazolo-[4,3-a][1,5]benzodiazepin-1,5-dione |
| 24. | 2-(methylthio)-3-methoxy-7-chloro-5-phenyl-3H-1,5-benzodiazepin-4-one | 4-methoxy-8-chloro-6-phenyl 1H-s-triazolo[4,3-a][1,5]-benzodiazepin-1,5-dione |
| 25. | 2-(methylthio)-8-methyl-5-phenyl-3H-1,5-benzodiazepin-4-one | 9-methyl-6-phenyl-1H-s-triazolo[4,3-a][1,5]benzodiazepin-1,5-dione |
| 26. | 2-(methylthio)-8-chloro-5-phenyl-3H-1,5-benzodiazepin-4-one | 9-chloro-6-phenyl-1H-s-triazolo[4,3-a][1,5]-benzodiazepin-1,5-dione |
| 27. | 2-(methylthio)-8-(trifluoromethyl)-5-phenyl-3H-1,5-benzodiazepin-4-one | 9-(trifluoromethyl)-6-phenyl-1H-s-triazolo[4,3-a]-[1,5]benzodiazepin-1,5-dione |

EXAMPLES 28-34

8-chloro-6-phenyl-1H-s-triazolo[4,3-a][1,5]benzodiazepine-1,5-dione

Following the procedure of Example 1, Method B, but substituting the alkyl carbazates indicated below for ethyl carbazate in Example 1, Method B, gives the title compound.

28. methyl carbazate
29. propyl carbazate
30. isopropyl carbazate
31. butyl carbazate
32. isobutyl carbazate
33. secondary butyl carbazate
34. n-hexyl carbazate

EXAMPLE 35

2-(Methylthio)-7-chloro-5-phenyl-3H-1,5-benzodiazepin-4-one

To 3.03 g of 7-chloro-5-phenyl-1H-1,5-benzodiazepin-4-one-2-thione in a solution of 0.40 g of sodium hydroxide and 15 ml of methanol is added, with stirring a solution of 1.4 g of methyl iodide in 10 ml of methanol. Stirring is continued for 1 hour, the reaction is then evaporated and suspended in methylene chloride (30 ml). The suspension is filtered through a short Florisil column; the column is washed with ethyl acetate and the combined filtrates are evaporated. The residue is triturated with a minimum amount of absolute ethanol and the title compound is filtered off and dried.

EXAMPLES 36-39

Following the procedure of Example 35 but substituting the compounds indicated in Column I below for methyl iodide and the compounds indicated in Column II for 7-chloro-5-phenyl-1H-1,5-benzodiazepin-4-one-2-thione in Example 35, the benzodiazepinones indicated in Column III are obtained.

| | I | II | III |
|---|---|---|---|
| 36. | benzylbromide | 7-(trifluoromethyl)-5-phenyl-1H-1,5-benzodiazepin-4-one-2-thione | 2-(benzylthio)-7-(trifluoromethyl)-5-phenyl-3H-1,5-benzodiazepin-4-one |

-continued

| | I | II | III |
|---|---|---|---|
| 37. | O-propyl p-toluene-sulfonate | 7-nitro-5-(o-chlorophenyl)-1H-1,5-benzodiazepin-4-one-2-thione | 2-(propylthio)-7-nitro-5-(o-chlorophenyl)-3H-1,5-benzodiazepin-4-one |
| 38. | methyl iodide | 7-(trifluoromethyl)-5-phenyl-1H-1,5-benzodiazepin-4-one-2-thione | 2-(methylthio)-7-(trifluoromethyl)-5-phenyl-3H-1,5-benzodiazepin-4-one |
| 39. | diethyl sulfate | 7-chloro-5-phenyl-1H-1,5-benzodiazepin-4-one-2-thione | 2-(ethylthio)-7-chloro-5-phenyl-3H-1,5-benzodiazepin-4-one |

EXAMPLES 40–65

Following the procedure of Example 35 but substituting the compounds indicated in Column I below for 7-chloro-5-phenyl-1H-1,5-benzodiazepin-4-one-2-thione in Example 35, the compounds indicated in Column II are obtained.

| | I | II |
|---|---|---|
| 40. | 5-phenyl-1H-1,5-benzodiazepin-4-one-2-thione | 2-(methylthio)-5-phenyl-3H-1,5-benzodiazepin-4-one |
| 41. | 7-(trifluoromethyl)-5-phenyl-1H-1,5-benzodiazepin-4-one-2-thione | 2-(methylthio)-7-(trifluoromethyl)-5-phenyl-3H-1,5-benzodiazepin-4-one |
| 42. | 7-nitro-5-phenyl-1H-1,5-benzodiazepin-4-one-2-thione | 2-(methylthio)-7-nitro-5-phenyl-3H-1,5-benzodiazepin-4-one |
| 43. | 7-methyl-5-phenyl-1H-1,5-benzodiazepin-4-one-2-thione | 2-(methylthio)-7-methyl-5-phenyl-3H-1,5-benzodiazepin-4-one |
| 44. | 7-methoxy-5-phenyl-1H-1,5-benzodiazepin-4-one-2-thione | 2-(methylthio)-7-methoxy-5-phenyl-3H-1,5-benzodiazepin-4-one |
| 45. | 7-(methylthio)-5-phenyl-1H-1,5-benzodiazepin-4-one-2-thione | 2,7-di(methylthio)-5-phenyl-3H-1,5-benzodiazepin-4-one |
| 46. | 7-pentyl-5-phenyl-1H-1,5-benzodiazepin-4-one-2-thione | 2-(methylthio)-7-pentyl-5-phenyl-3H-1,5-benzodiazepin-4-one |
| 47. | 7-pentoxy-5-phenyl-1H-1,5-benzodiazepin-4-one-2-thione | 2-(methylthio)-7-pentoxy-5-phenyl-3H-1,5-benzodiazepin-4-one |
| 48. | 7-bromo-5-phenyl-1H-1,5-benzodiazepin-4-one-2-thione | 2-(methylthio)-7-bromo-5-phenyl-3H-1,5-benzodiazepin-4-one |
| 49. | 7-fluoro-5-phenyl-1H-1,5-benzodiazepin-4-one-2-thione | 2-(methylthio)-7-fluoro-5-phenyl-3H-1,5-benzodiazepin-4-one |
| 50. | 7-cyano-5-phenyl-1H-1,5-benzodiazepin-4-one-2-thione | 2-(methylthio)-7-cyano-5-phenyl-3H-1,5-benzodiazepin-4-one |
| 51. | 7-chloro-5-(2-chlorophenyl)-1H-1,5-benzodiazepin-4-one-2-thione | 2-(methylthio)-7-chloro-5-(2-chlorophenyl)-3H-1,5-benzodiazepin-4-one |
| 52. | 7-chloro-5-(2-fluorophenyl)-1H-1,5-benzodiazepin-4-one-2-thione | 2-(methylthio)-7-chloro-5-(2-fluorophenyl)-3H-1,5-benzodiazepin-4-one |
| 53. | 7-chloro-5-(3-chlorophenyl)-1H-1,5-benzodiazepin-4-one-2-thione | 2-(methylthio)-7-chloro-5-(3-chlorophenyl)-3H-1,5-benzodiazepin-4-one |
| 54. | 7-chloro-5-(4-chlorophenyl)-1H-1,5-benzodiazepin-4-one-2-thione | 2-(methylthio)-7-chloro-5-(4-chlorophenyl)-3H-1,5-benzodiazepin-4-one |
| 55. | 7-chloro-5-(2-methoxyphenyl)-1H-1,5-benzodiazepin-4-one-2-thione | 2-(methylthio)-7-chloro-5-(2-methoxyphenyl)-3H-1,5-benzodiazepin-4-one |
| 56. | 7-chloro-5-(3-methoxyphenyl)-1H-1,5-benzodiazepin-4-one-2-thione | 2-(methylthio)-7-chloro-5-(3-methoxyphenyl)-3H-1,5-benzodiazepin-4-one |
| 57. | 7-chloro-5-(2-methylphenyl)-1H-1,5-benzodiazepin-4-one-2-thione | 2-(methylthio)-7-chloro-5-(2-methylphenyl)-3H-1,5-benzodiazepin-4-one |
| 58. | 7-chloro-5-(3-methylphenyl)-1H-1,5-benzodiazepin-4-one-2-thione | 2-(methylthio)-7-chloro-5-(3-methylphenyl)-3H-1,5-benzodiazepin-4-one |
| 59. | 7-chloro-5-(4-methylphenyl)-1H-1,5-benzodiazepin-4-one-2-thione | 2-(methylthio)-7-chloro-5-(4-methylphenyl)-3H-1,5-benzodiazepin-4-one |
| 60. | 3-methyl-7-chloro-5-phenyl-1H-1,5-benzodiazepin-4-one-2-thione | 2-(methylthio)-3-methyl-7-chloro-5-phenyl-3H-1,5-benzodiazepin-4-one |
| 61. | 3-(benzyloxy)-7-chloro-5-phenyl-1H-1,5-benzodiazepin-4-one-2-thione | 2-(methylthio)-3-(benzyloxy)-7-chloro-5-phenyl-3H-1,5-benzodiazepin-4-one |
| 62. | 3-methoxy-7-chloro-5-phenyl-1H-1,5-benzodiazepin-4-one-2-thione | 2-(methylthio)-3-methoxy-7-chloro-5-phenyl-3H-1,5-benzodiazepin-4-one |
| 63. | 8-methyl-5-phenyl-1H-1,5-benzodiazepin-4-one-2-thione | 2-(methylthio)-8-methyl-5-phenyl-3H-1,5-benzodiazepin-4-one |
| 64. | 8-chloro-5-phenyl-1H-1,5-benzodiazepin-4-one-2-thione | 2-(methylthio)-8-chloro-5-phenyl-3H-1,5-benzodiazepin-4-one |
| 65 | 8-(trifluoromethyl)-5-phenyl-1H-1,5-benzodiazepin-4-one-2-thione | 2-(methylthio)-8-(trifluoromethyl)-5-phenyl-3H-1,5-benzodiazepin-4-one |

EXAMPLE 66

7-chloro-5-phenyl-1H-1,5-benzodiazepin-4-one-2-thione

A solution of 28.6 g of 7-chloro-5-phenyl-1H-1,5-benzodiazepine-2,4-dione and 23.3 g of phosphorus pentasulfide in 250 ml of pyridine is refluxed, with stirring, for 40 minutes under argon. The solvent is evaporated in vacuo.

The residue is stirred in ice water and extracted with methylene chloride. The organic phase is washed consecutively with dilute aqueous hydrochloric acid, water and dried. The organic phase is filtered through a short column of neutral III alumina and the filtrate evaporated. The residue is triturated with a small amount of hot benzene and the product filtered off and dried.

EXAMPLE 67

8-chloro-6-(2',4'-dichlorophenyl)-1H-s-triazolo[4,3-a][1,5]benzodiazepine-1,5-dione

Part A 20 g of 2',4',5-trichloro-2-nitrodiphenylamine in 100 ml of methanol containing 0.2 g of Raney nickel is hydrogenated at an initial hydrogen pressure of 7 atm. until three molar equivalents of hydrogen is consumed. The suspension is filtered and the filtrate evaporated to give the 2',4',5-trichloro-2-aminodiphenylamine.

Part B

To a stirred refluxing solution of 28.7 g of the above produced 2',4',5-trichloro-2-aminodiphenylamine in 400 ml benzene is added, dropwise, a solution of 13.8 g of malonyl dichloride in 45 ml benzene. After addition is complete the reaction was refluxed for 7 hours, concentrated to ½ the original volume and cooled. The product, 7-chloro-(2',4'-dichlorophenyl)-1H-1,5-benzodiazepin-2,4-dione, is filtered off and dried.

Part C

Following the procedure of example 66 but substituting the above produced 7-chloro-5-(2',4'-dichlorophenyl)-1H-1,5-benzodiazepin-2,4-dione for 7-chloro-5- phenyl-1H-1,5-benzodiazepine-2,4-dione in example 66, gives 7-chloro-5-(2',4'-dichlorophenyl)-1H-1,5-benzodiazepin-4-one-2-thione.

the substituents and the position they occupy are indicated below:

| Example No. | 7 | 8 | 9 | 10 | 2' | 3' | 4' | 5' | 6' |
|---|---|---|---|---|---|---|---|---|---|
| 68. |  | Cl | Cl |  |  |  |  |  |  |
| 69. |  |  |  | Cl |  |  |  |  |  |
| 70. |  |  | Cl |  |  |  |  | $CH_3SO_2$ |  |
| 71. |  |  | $CF_3$ |  | Cl |  |  |  | $CF_3$ |
| 72. |  | Cl |  |  | $CH_3$ |  | $CH_3$ |  |  |
| 73. |  | Cl |  |  | $CH_3$ |  | Cl |  |  |
| 74. |  | Cl |  |  | $CH_3$ | $CH_3$ |  |  |  |
| 75. |  | Cl |  |  | Cl |  | $CH_3$ |  |  |
| 76. | Cl |  | Cl |  |  |  |  |  |  |
| 77. |  | $CH_3O$ | $CH_3O$ |  |  |  |  |  |  |
| 78. |  | Cl | Cl |  |  |  | Cl |  |  |
| 79. |  |  | Cl |  | $OCH_3$ |  |  | $OCH_3$ |  |
| 80. | Cl |  |  |  |  |  |  |  |  |
| 81. |  |  |  |  | Cl | Cl |  |  |  |
| 82. | $OCH_3$ |  |  | $OCH_3$ |  |  |  |  |  |
| 83. |  | $CH_3$ | Cl |  |  |  |  |  |  |
| 84. |  |  | $CH_3SO_2$ |  |  |  |  |  |  |
| 85. |  |  | Cl |  |  |  | $SCH_3$ |  |  |
| 86. |  |  | Cl |  |  |  | $CH_3SO_2$ |  |  |
| 87. |  | Cl |  |  | F |  |  |  | F |
| 88. |  |  | Cl |  | F |  |  |  | F |

Part D

Following the procedure of example 35 but substituting the above produced 7-chloro-5-(2',4'-dichlorophenyl)-1H-1,5-benzodiazepin-4-one-2-thione for 7-chloro-5-phenyl-1H-1,5-benzodiazepin-4-one-2-thione in example 35, gives 2-(methylthio)-7-chloro-5-(2',4'-dichlorophenyl)-3H-1,5-benzodiazepin-4-one.

Part E

Following the procedure of example 1, Method B, but substituting the above produced 2-(methylthio)-7-chloro-5-(2',4'-dichlorophenyl)-3H-1,5-benzodiazepin-4-one for 2-(methylthio)-7-chloro-5-phenyl-3H-1,5-benzodiazepin-4-one in example 1, Method B, gives the title compound of formula 1.

EXAMPLES 68–88

Following the procedure of part A to E of the foregoing example but employing as starting materials the substituted compounds of formula 10 wherein the substituents and the position they occupy are indicated below:

| Example No. | 3 | 4 | 5 | 6 | 2' | 3' | 4' | 5' | 6' |
|---|---|---|---|---|---|---|---|---|---|
| 68. |  | Cl | Cl |  |  |  |  |  |  |
| 69. | Cl |  |  |  |  |  |  |  |  |
| 70. |  | Cl |  |  |  |  |  | $CH_3SO_2$ |  |
| 71 |  | $CF_3$ |  |  | Cl |  |  |  | $CF_3$ |
| 72. |  |  | Cl |  | $CH_3$ |  | $CH_3$ |  |  |
| 73. |  |  | Cl |  | $CH_3$ |  | Cl |  |  |
| 74. |  |  | Cl |  | $CH_3$ | $CH_3$ |  |  |  |
| 75. |  |  | Cl |  | Cl |  |  |  |  |
| 76. |  | Cl |  | Cl |  |  |  |  |  |
| 77. |  | $CH_3O$ | $CH_3O$ |  |  |  |  |  |  |
| 78. |  | Cl | Cl |  |  |  | Cl |  |  |
| 79. |  | Cl |  |  | $OCH_3$ |  |  | $OCH_3$ |  |
| 80. |  |  |  | Cl |  |  |  |  |  |
| 81. |  |  |  |  | Cl | Cl |  |  |  |
| 82. | $CH_3O$ |  |  | $CH_3O$ |  |  |  |  |  |
| 83. |  | Cl | $CH_3$ |  |  |  |  |  |  |
| 84. |  | $CH_3SO_2$ |  |  |  |  |  |  |  |
| 85. |  | Cl |  |  | $CH_3S$ |  |  |  |  |
| 86. |  | Cl |  |  | $CH_3SO_2$ |  |  |  |  |
| 87. |  |  | Cl |  | F |  |  |  | F |
| 88. |  | Cl |  |  | F |  |  |  | F | there is obtained the correspondingly substituted compound of formula I wherein $R^1$=hydrogen and wherein

EXAMPLE 89

4-Hydroxy-8-chloro-6-phenyl-1H-s-triazolo-[4,3-a][1,5]benzodiazepine-1,5-dione 44.6 g of 4-(benzyloxy)-8-chloro-6-phenyl-1H-s-triazolo[4,3-a][1,5]benzodiazepine-1,5-dione in 400 ml of ethanol containing 2.0 g of 10% palladium-on-charcoal is hydrogenated at an initial hydrogen pressure of 40 p.s.i. After 0.1 mole of hydrogen has been absorbed, the reaction is stopped, filtered and the solvent evaporated. The residue is triturated with ether and the title compound filtered off and dried.

EXAMPLE 90

8-(methylsulfinyl)-6-phenyl-1H-s-triazolo[4,3-a][1,5]-benzodiazepine-1,5-dione 3.22 g of 8-(methylthio)-6-phenyl-1H-s-triazolo [4,3-a][1,5]benzodiazepine-1,5-dione and 2.14 g of sodium metaperiodate in 500 ml methanol is stirred at +5° C for 24 hours. The reaction is evaporated; the residue dissolved in methylene chloride, washed with water, dried and concentrated. The concentrate is chromatographed on twenty silica gel (1000μ plates, 20 × 20 cm) using acetone-methanol (9:1) as eluting solvent. The band containing the product is removed, stirred with acetone-methanol (4:1) and the silica gel filtered off. The filtrate is evaporated to give the title compound.

EXAMPLE 91

8-amino-6-phenyl-1H-s-triazolo[4,3-a][1,5]benzodiazepine-1,5-dione 33.5 g of 8-nitro-6-phenyl-1H-s-triazolo[4,3-a][1,5]benzodiazepine-1,5-dione in 100 ml of ethanol containing 2.0 g of 10% palladium-on-charcoal is hydrogenated at room temperature at an initial hydrogen pressure of 50 p.s.i. The reaction is stopped when 0.3 moles of hydrogen has been absorbed; the suspension is filtered and the filtrate evaporated to give the title compound.

EXAMPLE 92

8-acetamido-6-phenyl-1-H-s-triazolo[4,3-a][1,5]benzodiazepine-1,5-dione 2.91 g of 8-amino-6-phenyl-1H-s-triazolo[4,3-a][1,5]benzodiazepine-1,5-dione and 1.02 g of acetic anhydride in 50 ml pyridine is stirred for 12 hours then refluxed for 30 minutes. The reaction is evaporated; the residue is taken up in chloroform, washed with dilute aqueous sodium bicarbonate, with water and dried. The solvent is evaporated to give the title compound.

EXAMPLE 93

8-(methylsulfonyl)-6-phenyl-1H-s-triazolo[4,3-a][1,5]benzodiazepine-1,5-dione

Following the procedure of example 90, but using 4.14 g instead of 2.14 g of sodium metaperiodate, the title compound is obtained.

EXAMPLE 94

2-Methyl-8-chloro-6-phenyl-1H-s-triazolo[4,3-a][1,5]benzodiazepin-1,5-dione

To an ice-cooled, stirred solution of 3.7 g of 8-chloro-6-phenyl-1H-s-triazolo[4,3-a][1,5]benzodiazepine-1,5-dione in 100 ml of dried and distilled 1,2-dimethoxyethane is added, in a portionwise manner, 0.57 g of a 57% dispersion of sodium hydride in mineral oil. After the evolution of hydrogen has ceased (15 min), a solution of 1.79 g (0.014 mole) of methyl iodide is added, the ice bath removed and stirring continued at room temperature for 2 hours, followed by heating under reflux for 1 hour. The solvent is then removed by distillation. The residue is dissolved in 100 ml of chloroform, washed twice with 100 ml portions of water, dried and concentrated. Treatment of the residue with a small amount of ether precipitates the title compound which is filtered off, dried and recrystallized from ethyl acetate.

EXAMPLE 95 – 101

Following the procedure of example 94 but substituting the compounds indicated in column I below for methyl iodide in example 94, the compounds indicated in column II are obtained:

| | I | II |
|---|---|---|
| 95. | 3-dimethylaminopropyl chloride | 2-(3-dimethylaminopropyl)-8-chloro-6-phenyl-1H-s-triazolo[4,3-a][1,5]benzodiazepine-1,5-dione |
| 96. | 2-diethylaminoethyl bromide | 2-(2-diethylaminoethyl)-8-chloro-6-phenyl-1H-s-triazolo[4,3-a][1,5]benzodiazepine-1,5-dione |
| 97. | 2-dimethylaminoethyl chloride | 2-(2-dimethylaminoethyl)-8-chloro-6-phenyl-1H-s-triazolo[4,3-a][1,5]benzodiazepine-1,5-dione |
| 98. | 3-diethylaminopropyl chloride | 2-(3-diethylaminopropyl)-8-chloro-6-phenyl-1H-s-triazolo[4,3-a][1,5]benzodiazepine-1,5-dione |
| 99. | Benzyl bromide | 2-benzyl-8-chloro-6-phenyl-1H-s-triazolo[.4,3-a][1,5]benzodiazepin-1,5-dione |
| 100. | p-chlorophenethyl chloride | 2-(p-chlorophenethyl)-8-chloro-6-phenyl-1H-s-triazolo[4,3-a]-[1,5]benzodiazepine-1,5-dione |
| 101. | 2-(N-benzyl-N-methylamino)ethyl chloride | 2-[2-(N-benzyl-N-methylamino)-ethyl]-8-chloro-6-phenyl-1H-s-triazolo[4,3-a][1,5]benzodiazepine-1,5-dione |
| 102. | 3-[(t-butoxycarbonyl)-amino]propyl chloride | 2-[3-[(t-butoxycarbonyl)amino]-propyl]-8-chloro-6-phenyl-1H-s-triazolo[4,3-a][1,5]benzodiazepine-1,5-dione |

EXAMPLE 103

2-(2-Methylaminopropyl)-8-chloro-6-phenyl-1H-s-triazolo[4,3-a][1,5]benzodiazepine-1,5-dione 4 g of 2-[2-(N-benzyl-N-methylamino)ethyl]-8-chloro-6-phenyl-1H-s-triazolo[4,3-a][1,5]benzodiazepine-1,5-dione in 100 ml of ethanol containing 0.4 g of 5% palladium on charcoal is hydrogenated at 50 p.s.i. hydrogen pressure until 1 molar equivalent of hydrogen is absorbed. The suspension is filtered and the filtrate is evaporated. The residue is triturated with a small amount of cold ether and the title compound is filtered off and dried.

EXAMPLE 104

2-(3-aminopropyl)-8-chloro-6-phenyl-1H-s-triazolo[4,3-a][1,5]benzodiazepine-1,5-dione 2.5 g of 2-[3-(t-butoxycarbonylamino)propyl]-8-chloro-6-phenyl-1H-s-triazolo[4,3-a][1,5]benzodiazepine-1,5-dione in 50 ml of trifluoroacetic acid is stirred at room temperature for 2 hours. The reaction is evaporated and the residue is stirred with a solution of 1.9 g of sodium bicarbonate in 400 ml of methanol-water (10:1). After 3 hours the reaction is evaporated and the residue is partitioned between methylene chloride and water. The methylene chloride is washed with water, dried and evaporated to give the title compound.

EXAMPLES 105 – 111

Following the procedure of Example 94 but substituting the compounds indicated in Column I below for 8-chloro-6-phenyl-1H-s-triazolo[4,3-a][1,5]benzodiazephine-1,5-dione in Example 94, the compounds indicated in Column II are obtained.

| | I | II |
|---|---|---|
| 105. | 6-phenyl-1H-s-triazolo-[4,3-a][1,5]benzodiazepine-1,5-dione | 2-methyl-6-phenyl-1H-s-triazolo[4,3-a][1,5]benzodiazepine-1,5-dione |
| 106. | 8-trifluoromethyl)-6-phenyl-1H-s-triazolo-[4,3-a][1,5]benzodiazepine-1,5-dione | 2-methyl-8-(trifluoromethyl)-6-phenyl-1H-s-triazolo[4,3-a]-[1,5]benzodiazepine-1,5-dione |
| 107. | 8-nitro-6-phenyl-1H-s-triazolo[4,3-a][1,5]-benzodiazepine-1,5-dione | 2-methyl-8-nitro-6-phenyl-1H-s-triazolo[4,3-a][1,5]-benzodiazepine-1,5-dione |
| 108. | 8-methyl-6-phenyl-1H-s-triazolo[4,3-a][1,5]-benzodiazepine-1,5-dione | 2,8-dimethyl-6-phenyl-1H-s-triazolo[4,3-a][1,5]-benzodiazepine-1,5-dione |

-continued

| | I | II |
|---|---|---|
| 109. | 8-methoxy-6-phenyl-1H-s-triazolo[4,3-a][1,5]-benzodiazepine-1,5-dione | 2-methyl-8-methoxy-6-phenyl-1H-s-triazolo[4,3-a][1,5]-benzodiazepine-1,5-dione |
| 110. | 8-(methylthio)-6-phenyl-1H-s-triazolo[4,3-a][1,5]benzodiazepine-1,5-dione | 2-methyl-8-(methylthio)-6-phenyl-1H-s-triazolo[4,3-a][1,5]benzodiazepine-1,5-dione |
| 111. | 4-benzyloxy-8-chloro-6-phenyl-1H-s-triazolo[4,3-a][1,5]benzodiazepine-1,5-dione | 2-methyl-(4-benzyloxy-8-chloro)-6-phenyl-1H-s-triazolo[4,3-a][1,5]benzodiazepine-1,5-dione |

EXAMPLE 112

2-Methyl-4-hydroxy-6-phenyl-1H-s-triazolo[4,3-a][1,5]benzodiazepine-1,5-dione

Following the procedure of example 89 but substituting 2-methyl-4-(benzyloxy)-8-chloro-6-phenyl-1H-s-triazolo[4,3-a][1,5]benzodiazepine-1,5-dione for 4-(benzyloxy)-8-chloro-6-phenyl-1H-s-triazolo[4,3-a][1,5]benzodiazepine-1,5-dione in Example 89, the title compound is obtained.

EXAMPLE 113

4-acetoxy-8-chloro-6-phenyl-1H-s-triazolo[4,3-a][1,5]benzodiazepine-1,5-dione 3.4 g of 4-hydroxy-8-chloro-6-phenyl-1H-s-triazolo[4,3-a][1,5]benzodiazepine-1,5-dione and 1.0 g of acetic anhydride in 10 ml of pyridine are warmed in a steam bath for 0.2 hour and stirred at room temperature for 10 hours. The reaction mixture is cooled, diluted with 100 ml of methylene chloride and washed with 100 ml water containing 0.84 g sodium bicarbonate. The organic phase is washed four times with water, dried and evaporated. The residue is triturated with a minimum amount of ether and the title compound filtered off, dried and recrystallized from methylene chloride and ether.

EXAMPLE 114

8-chloro-2,6-diphenyl-1H-s-triazolo[4,3-a][1,5]benzodiazepine-1,5-dione

A mixture of 8.2 g of 8-chloro-6-phenyl-1H-s-triazolo[4,3-a][1,5]benzodiazepine-1,5-dione, 5 g of copper powder and 2.5 g of potassium acetate in 100 ml of bromobenzene are refluxed for 6 hours with stirring. The reaction is diluted with methylene chloride, filtered through a short Florisil column and the filtrate washed with dilute aqueous ammonium hydroxide. The organic phase is washed with water, dried and the solvent evaporated to give the title compound.

EXAMPLES 115 – 119

Following the procedure of example 114 but substituting the compounds indicated in Column I below for 8-chloro-6-phenyl-1H-s-triazolo[4,3-a][1,5]benzodiazepine-1,5-dione in Example 114, the compounds indicated in Column II are obtained.

| | I | II |
|---|---|---|
| 115. | 8-(trifluoromethyl)-6-phenyl-1H-s-triazolo[4,3-a][1,5]benzodiazepine-1,5-dione | 8-(trifluoromethyl)-2,6-diphenyl-1H-s-triazolo[4,3-a][1,5]benzodiazepine-1,5-dione |
| 116. | 8-nitro-6-phenyl-1H-s-triazolo[4,3-a][1,5]-benzodiazepine-1,5-dione | 8-nitro-2,6-diphenyl-1H-s-triazolo[4,3-a][1,5]-benzodiazepine-1,5-dione |
| 117. | 8-bromo-6-phenyl-1H-s-triazolo[4,3-a][1,5]-benzodiazepine-1,5-dione | 8-bromo-2,6-diphenyl-1H-s-triazolo[4,3-a][1,5]-benzodiazepine-1,5-dione |
| 118. | 9-chloro-6-phenyl-1H-s-triazolo[4,3-a][1,5]-benzodiazepine-1,5-dione | 9-chloro-2,6-diphenyl-1H-s-triazolo[4,3-a][1,5]-benzodiazepine-1,5-dione |
| 119. | 8-chloro-6-(o-chlorophenyl)-1H-s-triazolo-[4,3-a][1,5]benzodiazepine-1,5-dione | 8-chloro-2-phenyl-6-(o-chlorophenyl)-1H-s-triazolo-[4,3-a][1,5]benzodiazepine-1,5-dione |

EXAMPLES 120 – 124

Following the procedure of Example 114 but substituting the compounds indicated in Column I below for 8-chloro-6-phenyl-1H-s-triazolo[4,3-a][1,5]benzodiazepine-1,5-dione in example 114, and substituting o-chlorobromobenzene for bromobenzene in example 114, the compounds indicated in Column II are obtained.

| | I | II |
|---|---|---|
| 120. | 8-chloro-6-phenyl-1H-s-triazolo[4,3-a][1,5]-benzodiazepine-1,5-dione | 8-chloro-2-(o-chlorophenyl)-6-phenyl-1H-s-triazolo[4,3-a]-[1,5]benzodiazepine-1,5-dione |
| 121. | 8-(trifluoromethyl)-6-phenyl-1H-s-triazolo-[4,3-a][1,5]benzodiazepine-1,5-dione | 8-(trifluoromethyl)-2-(o-chlorophenyl)-6-phenyl-1H-s-triazolo[4,3-a][1,5]-benzodiazepine-1,5-dione |
| 122. | 8-nitro-6-phenyl-1H-s-triazolo[4,3-a][1,5]-benzodiazepine-1,5-dione | 8-nitro-2-(o-chlorophenyl)-6-phenyl-1H-s-triazolo-[4,3-a][1,5]benzodiazepine-1,5-dione |
| 123. | 8-bromo-6-phenyl-1H-s-triazolo[4,3-a][1,5]-benzodiazepine-1,5-dione | 8-bromo-2-(o-chlorophenyl)-6-phenyl-1H-s-triazolo-[4,3-a][1,5]benzodiazepine-1,5-dione |
| 124. | 8-chloro-6-(o-chlorophenyl)-1H-s-triazolo-[4,3-a][1,5]benzodiazepine-1,5-dione | 8-chloro-2,6-di(o-chlorophenyl)-1H-s-triazolo[4,3-a]-[1,5]benzodiazepine-1,5-dione |

EXAMPLE 125

3-(7-chloro-5-phenyl-3H-1,5-benzodiazepin-4-one-2-yl)carbazic acid ethyl ester

Method A 3.2 g of 2-(methylthio)-7-chloro-5-phenyl-1H-1,5-benzodiazepin-4-one and 1.8 g of ethyl carbazate in 100 ml ethanol is refluxed for 14 hours. During this time a slow stream of nitrogen is bubbled through the reaction mixture. The mixture is evaporated, the residue taken up in methylene chloride, washed with water, dried and the solvent evaporated. The residue is chromatographed on 10 1000μ silica gel plates (20 × 20 cm) with acetone-methanol (9:1) eluant. The band containing the product is removed and stirred with acetone-methanol (4:1). The silica gel is filtered off and the filtrate evaporated to give the title compound.

Method B 2.8 g of 2-hydrazino-7-chloro-5-phenyl-3H-1,5-benzodiazepin-4-one and 1.1 g of ethyl chloroformate in 25 ml of triethylamine is stirred at room temperature for 10 hours. The reaction mixture is evaporated and partitioned between 100 ml methylene chloride and a solution of 0.84 g sodium bicarbonate in 50 ml water. The organic phase is dried and evaporated.

EXAMPLE 126

Preparation of Capsule Formulation

| Ingredient | Milligrams per Capsule |
|---|---|
| 8-chloro-6-phenyl-1H-s-triazolo-[4,3-a][1,5]benzodiazepine-1,5-dione | 400 |
| Starch | 80 |
| Magnesium stearate | 5 |

The active ingredient, starch and magnesium stearate are blended together. The mixture is used to fill hard shell capsules of a suitable size at a fill weight of 485 milligrams per capsule.

EXAMPLE 127

Preparation of Tablet Formulation

| Ingredient | Milligrams per Tablet |
|---|---|
| 8-chloro-6-(2'-chlorophenyl)-1H-s-triazolo[4,3-a][1,5]benzodiazepine-1,5-dione. | 300 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 300 milligrams of active ingredient.

EXAMPLE 128

Preparation of Oral Syrup Formulation

| Ingredient | Amount |
|---|---|
| 2-Methyl-8-chloro-6-phenyl-1H-s-triazolo-[4,3-a][1,5]benzodiazepin-1,5-dione | 500 mg. |
| Sorbitol solution (70% N.F.) | 40 ml. |
| Sodium benzoate | 150 mg. |
| Sucaryl | 90 mg. |
| Saccharin | 10 mg. |
| Red Dye (F.D. & Co. No. 2) | 10 mg. |
| Cherry flavor | 50 mg. |
| Distilled water    qs to | 100 ml. |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

What is claimed is:

1. A compound of the formula

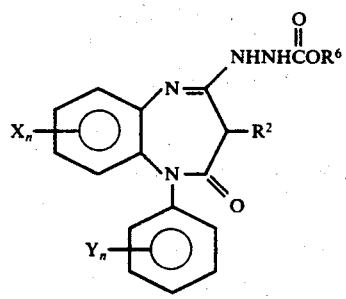

wherein
$R^2$ is H, alkyl of 1–3 carbons, hydroxy or alkanoyloxy of 1–4 carbons;
X and Y are the same or different and are H, F, Cl, Br, trifluoromethyl, alkyl of 1 to 4 carbons, alkoxy of 1–4 carbons, nitro, cyano, amino, alkanoylamino of 1–4 carbons, alkylthio of 1–4 carbons, alkylsulfinyl of 1–4 carbons or alkyl sulfonyl of 1–4 carbons;
$n$ is 0, 1 or 2;
and $R^6$ is alkyl of 1–4 carbons optionally substituted by phenyl.

2. The compound of claim 1 wherein $R^2$ is hydrogen or alkyl.

3. The compound as defined in claim 1 wherein X where present occupies the 7- or 8-position and Y where present occupies the 2'- or 6'-position.

4. A compound of claim 1 wherein $n$ is 1 and X occupies the 8-position and is chloro or bromo, trifluoromethyl or nitro.

5. A compound of claim 1 wherein $n$ is 1 and Y occupies the 2'-position and is chloro or fluoro, or wherein $n$ is 2 and Y occupies the 2'- and 6'-positions and is fluoro in each case.

6. A compound of claim 1 wherein $R^2$ is H, $n$ is 1 and X occupies the 8-position and is chloro, bromo, trifluoromethyl or nitro.

* * * * *

UNITED STATES PATENT OFFICE
CERTIFICATE OF CORRECTION

Patent No. 4,070,355   Dated January 24, 1978

Inventor(s) B. Richard Vogt

It is certified that error appears in the above-identified patent and that said Letters Patent are hereby corrected as shown below:

Column 1, structure 1 should read as follows:

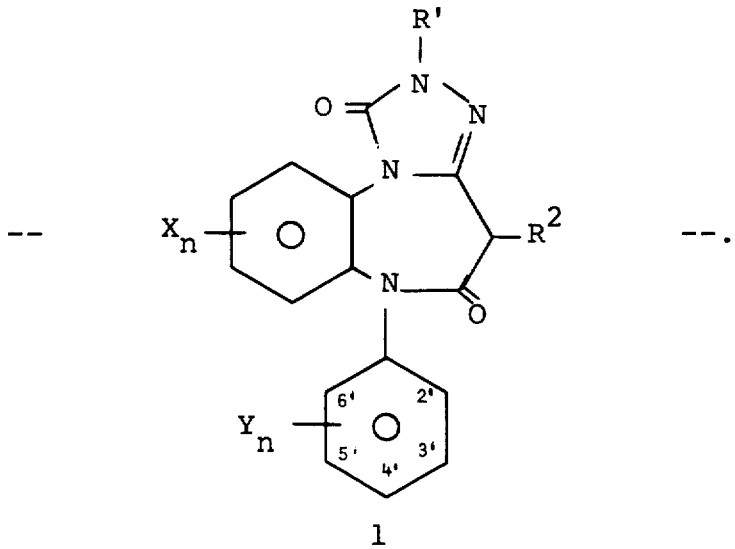

Signed and Sealed this

Thirtieth Day of May 1978

[SEAL]

Attest:

RUTH C. MASON
Attesting Officer

LUTRELLE F. PARKER
Acting Commissioner of Patents and Trademarks